US008226892B2

(12) United States Patent
Wilbertz et al.

(10) Patent No.: US 8,226,892 B2
(45) Date of Patent: Jul. 24, 2012

(54) GAS SENSOR

(75) Inventors: Christoph Wilbertz, Gundelfingen (DE); Heinz-Peter Frerichs, St. Peter (DE); Christoph Senft, München (DE)

(73) Assignee: Micronas GmbH, Freiburg I.Br. (DE)

( * ) Notice: Subject to any disclaimer, the term of this patent is extended or adjusted under 35 U.S.C. 154(b) by 416 days.

(21) Appl. No.: 12/411,163

(22) Filed: Mar. 25, 2009

(65) Prior Publication Data

US 2009/0246084 A1 Oct. 1, 2009

(30) Foreign Application Priority Data

Mar. 26, 2008 (EP) ..................................... 08005615

(51) Int. Cl.
*G01N 15/06* (2006.01)
*G01N 33/00* (2006.01)
*G01N 33/48* (2006.01)

(52) U.S. Cl. ............................... 422/83; 422/50; 422/98

(58) Field of Classification Search .................... 422/50, 422/83, 98

See application file for complete search history.

(56) References Cited

U.S. PATENT DOCUMENTS

| 4,303,612 | A | * | 12/1981 | Sonley | ............................. 422/94 |
| 5,367,283 | A | * | 11/1994 | Lauf et al. | ........................ 338/34 |
| 5,522,980 | A | * | 6/1996 | Hobbs et al. | .................. 204/432 |
| 6,447,658 | B1 | * | 9/2002 | Wu et al. | ........................ 204/424 |
| 6,634,213 | B1 | * | 10/2003 | O'Connor et al. | ........... 73/31.06 |
| 7,918,123 | B2 | * | 4/2011 | Wilbertz et al. | ............. 73/31.06 |
| 2004/0173004 | A1 | | 9/2004 | Eblen, Jr. et al. | |
| 2006/0196246 | A1 | | 9/2006 | Li et al. | |

FOREIGN PATENT DOCUMENTS

DE 43 33 875 A1 4/1995
EP 1 879 023 A1 1/2008

OTHER PUBLICATIONS

European Search Report, Sep. 1, 2008.
T. Galonska, et al., Cross Sensitivity and Stability of FET-Based Hydrogen Sensors, IEEE Sensors 2007 Conference.

* cited by examiner

*Primary Examiner* — Brian J Sines
(74) *Attorney, Agent, or Firm* — Muncy, Geissler, Olds & Lowe, PLLC

(57) ABSTRACT

A gas sensor has a gas-sensitive layer with a surface area where the electron affinity depends on the concentration of a target gas brought in contact with the surface area. An electrical potential sensor is capacitively coupled to the surface area via an air gap. The surface area of the gas-sensitive layer is covered by an electric insulating layer that is inert to the target gas and is bonded to the gas-sensitive layer. The coating is designed in such a way that it is permeable for the target gas and a different, non-target gas that can be adsorbed on the surface area. The coating has different diffusion constants for the target gas and the non-target gas. The diffusion constants are coordinated with each other in such a way that the sensitivity of the gas sensor to the target gas increases when the target gas concentration exceeds a predetermined concentration threshold in the presence of the non-target gas.

14 Claims, 6 Drawing Sheets

GAS SENSOR

Figure 1:
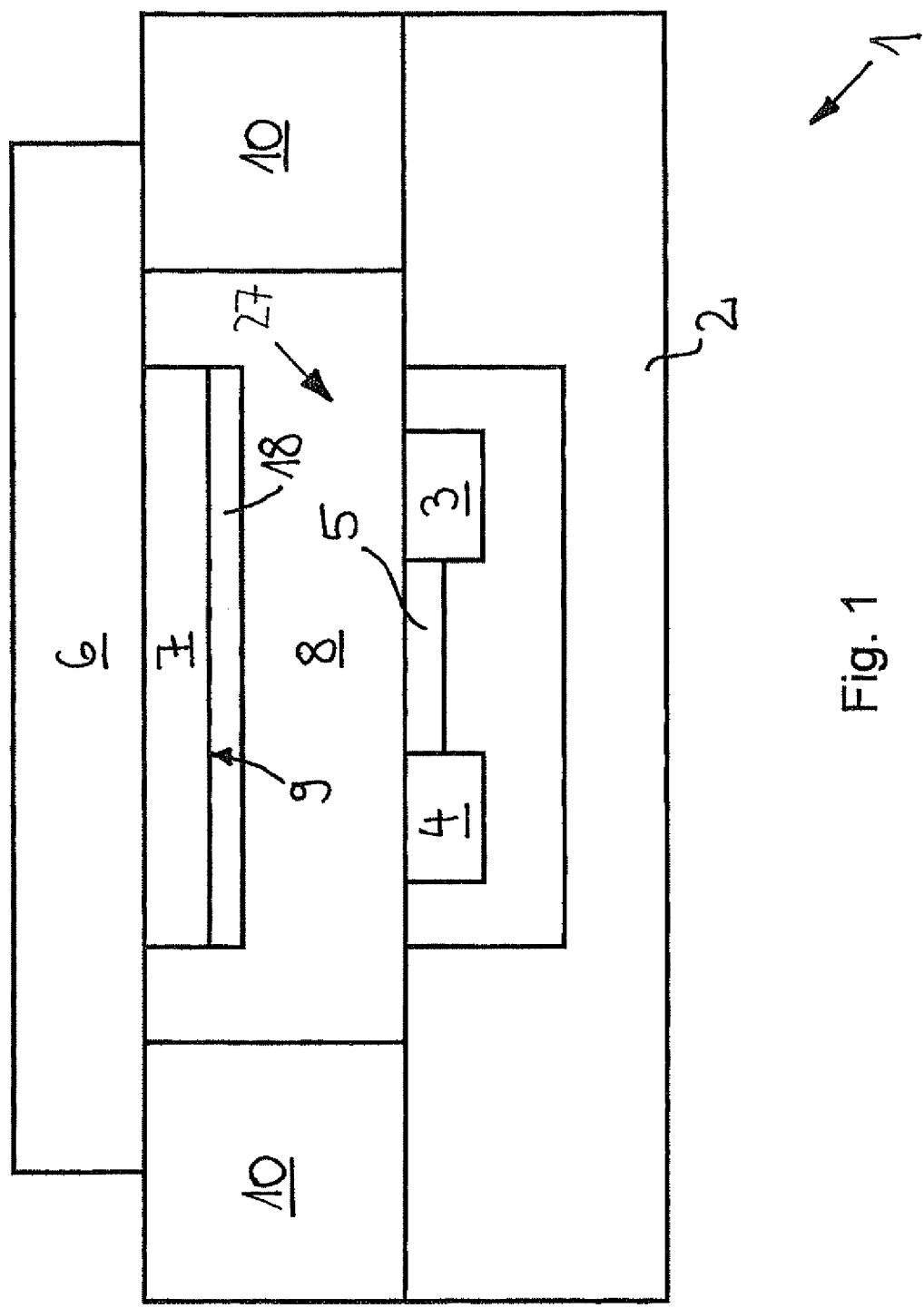

The invention relates to a gas sensor with at least one gas-sensitive layer, having at least one surface area, in which the electron affinity depends on the concentration of a target gas coming in contact with the surface area, and with at least one potential sensor capacitively coupled to the surface area via an air gap.

Such a gas sensor for the measurement of hydrogen gas concentrations is disclosed in DE 43 33 875 C2. The gas sensor has a silicon substrate in which a field effect transistor is integrated. The field effect transistor has a gate electrode that is conductively connected to a sensor electrode, over which a gas-sensitive layer is arranged, separated from the sensor electrode by an air gap and capacitively coupled to the sensor electrode via the air gap. A cover electrode is applied on the reverse side of the gas-sensitive layer opposite the sensor electrode. A surface area of the gas-sensitive layer opposite the sensor electrode comes in contact with the target gas, which is adsorbed upon contact with the surface area. When there is a change in the concentration of the target gas, the electron affinity in the surface area of the gas-sensitive layer changes. Because the sensor electrode is capacitively coupled to the surface area, the electrical potential at the gate electrode also changes. Depending on the change in potential, the current is guided between the drain and source terminal of the field effect transistor.

In normal, ambient air, a thin layer of atmospheric oxygen is dissociatively adsorbed on the surface of the gas-sensitive layer, i.e. as oxygen atoms, not oxygen molecules as they occur in the air. If the target gas enters the vicinity of the gas-sensitive layer, the target gas is first adsorbed on the surface, whereby the particular gas partially displaces the atmospheric oxygen previously adsorbed on the surface and assumes its adsorption positions. Both effects, the adsorption of the target gas and reduction of oxygen, additionally contribute to the change in surface electron affinity. Simultaneously, however, a reaction between hydrogen and oxygen takes place on the surface, aided by the catalytic effect of the gas-sensitive layer, creating water. At low temperatures below approx. 60° C., this causes only the surface hydrogen layer to gradually diminish; at higher temperatures, above approx. 60° C., this reaction occurs so quickly that it additionally causes the concentration of hydrogen in the immediate vicinity of the gas-sensitive layer to diminish as well. This allows the oxygen layer on the surface to increase again. All three effects distort the electron affinity in the opposing direction. This reaction can take place over hours or even seconds, depending on the temperature of the gas-sensitive layer, which can drastically disturb the measurement signal. Furthermore, the gas sensor's sensitivity towards the target gas decreases logarithmically when the target gas concentration increases. Analysis of the gas sensor measurement signal is therefore especially difficult with higher target gas concentrations.

Object of the invention is to create a gas sensor of the type described above that makes it possible to measure a predetermined target gas concentration with great precision.

This object is achieved for the invention wherein the surface area of the gas-sensitive layer is covered by an electric insulating layer that is inert to the target gas and is bonded to the gas-sensitive layer and is designed so as to be permeable to the target gas and a different, non-target gas that can adsorb on the surface area, so that the coating for the target gas and the non-target gas exhibit different diffusion constants and that the diffusion constants are coordinated in such a way so that the measurement sensitivity of the gas sensor increases for the target gas when the target gas concentration, in the presence of the non-target gas, crosses a predetermined concentration threshold. The term "measurement sensitivity" refers to the amount of change in the sensor signal of the potential sensor divided by the amount of change in the gas concentration after the abatement of possible transient signal particles contained in the measurement signal.

Surprisingly, it has been determined that with the gas sensor according to the invention, the sensitivity to the target gas increases drastically when, in the presence of a nearly constant concentration of the non-target gas, it crosses the concentration threshold. In a corresponding manner, the sensitivity to the target gas decreases drastically when the target gas, in the presence of a nearly constant concentration of the non-target gas, falls below the concentration threshold. Furthermore, coating disturbances in the measurement signal of the gas sensor that can be traced back to the interplay between target gas and non-target gas can be largely avoided. Advantageously, this enables the very precise detection of whether the target gas concentration lies above or below the concentration threshold. The gas sensor can particularly be used as a gas leak sensor.

In a preferred embodiment of the invention, the coating should contain at least one polymer. With this type of coating, a gas sensor using a gas-sensitive layer of platinum in a 1-4% concentration range for the detection of the target gas hydrogen can attain a high level of sensitivity. The polymer can be a polyimide, for example.

It is especially advantageous if the polymer is polymethylmethacrylate (PMMA). An almost abrupt increase in the sensor signal of the potential sensor can be achieved when the concentration threshold is crossed with a gas sensor with this coating. Furthermore, it has been determined that the gas sensor with this coating has long-term stability at high temperatures up to approx. 180° C. and/or in damp conditions.

It is advantageous if the coating is a lacquer. The coating can then be inexpensively applied to the gas-sensitive layer during manufacture of the gas sensor.

In a preferred embodiment of the invention, the thickness of the coating is between 0.3 µm and 4 µm, particularly between 0.5 µm and 2.5 µm. This layer thickness enables a favorable measurement signal characteristic for the gas sensor of the target gas.

In an advantageous embodiment of the invention, the level of the concentration threshold is dependent upon the temperature of the gas-sensitive layer and coating and the gas sensor has a temperature control unit, preferably a heater, for setting the temperature of the gas-sensitive layer and coating. Through heating and/or cooling of the gas-sensitive layer, the concentration threshold can be set to a desired level.

In a further modification of the invention, the gas sensor has a control device with an actual value entry connected to the potential sensor, a set point entry connected to a set point device, and a control signal output connected to the temperature control unit, whereby, in order to customize the concentration threshold to the target gas concentration, a set point can be assigned to the set point entry with the help of the set point device, whose value corresponds to the sensor signal of the potential sensor at the concentration threshold and/or has a target gas concentration above the concentration threshold. Different target gas concentrations can thus be measured with great precision, the concentration threshold being set so that each threshold agrees with or is slightly smaller than the target gas concentration.

In a preferred embodiment of the invention, the gas-sensitive layer is made of platinum or palladium. The gas sensor then has a high level of detection sensitivity towards the target gas hydrogen.

The potential sensor is preferably a field effect transistor with a substrate to which a drain and a source are attached, whereby a channel is formed between drain and source and whereby the channel is capacitively coupled to the surface area of the gas-sensitive layer, either directly via the air gap or indirectly via a gate electrode acting with the channel and with a sensor electrode conductively connected to the gate electrode. The field effect transistor can thus be a SGFET or a CCFET. Thereby, the gas sensor can have a compact design and can furthermore be easily integrated in a semiconductor chip. Thus, an evaluation device can also be integrated into the semiconductor chip to process the measurement signals of the gas sensor.

In another advantageous embodiment of the invention, the gas sensor is designed as a Kelvin probe, in which the potential sensor is capacitively coupled to the surface area of the gas-sensitive layer via an electrode that can move towards and away from the gas-sensitive layer and is separated from the surface area of the gas-sensitive layer by the air gap. Thereby, the electrode can, for example, be positioned relative to the gas-sensitive layer and brought to oscillate by means of a Piezo actuator. The potential sensor is assigned an evaluation and piloting device, that feeds a counter voltage to the electrode chosen so that the potential measured by the potential sensor averages zero. The counter voltage is a gauge for the concentration of the target gas in contact with the surface area of the gas-sensitive layer.

Figure 2:
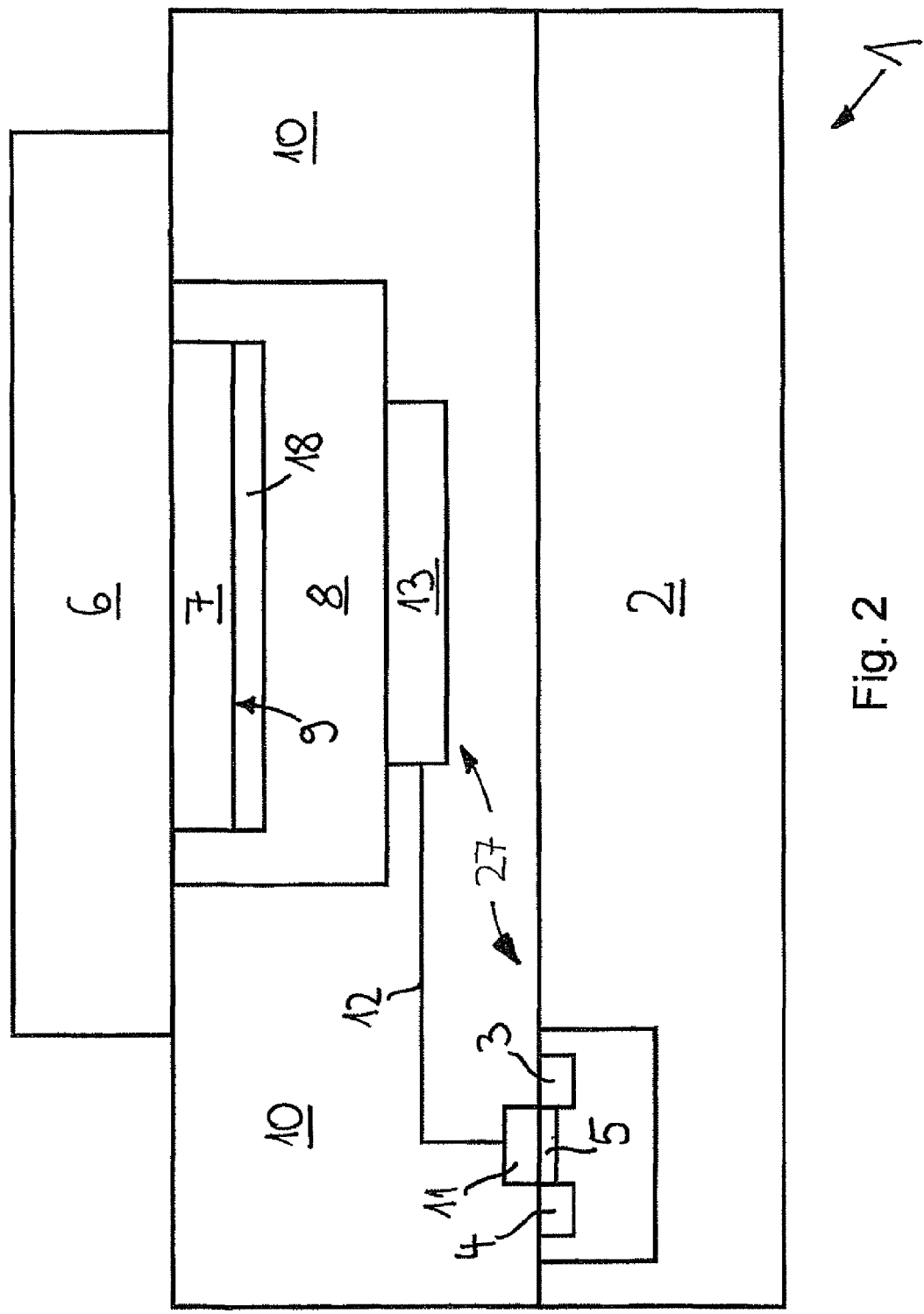
Figure 3:
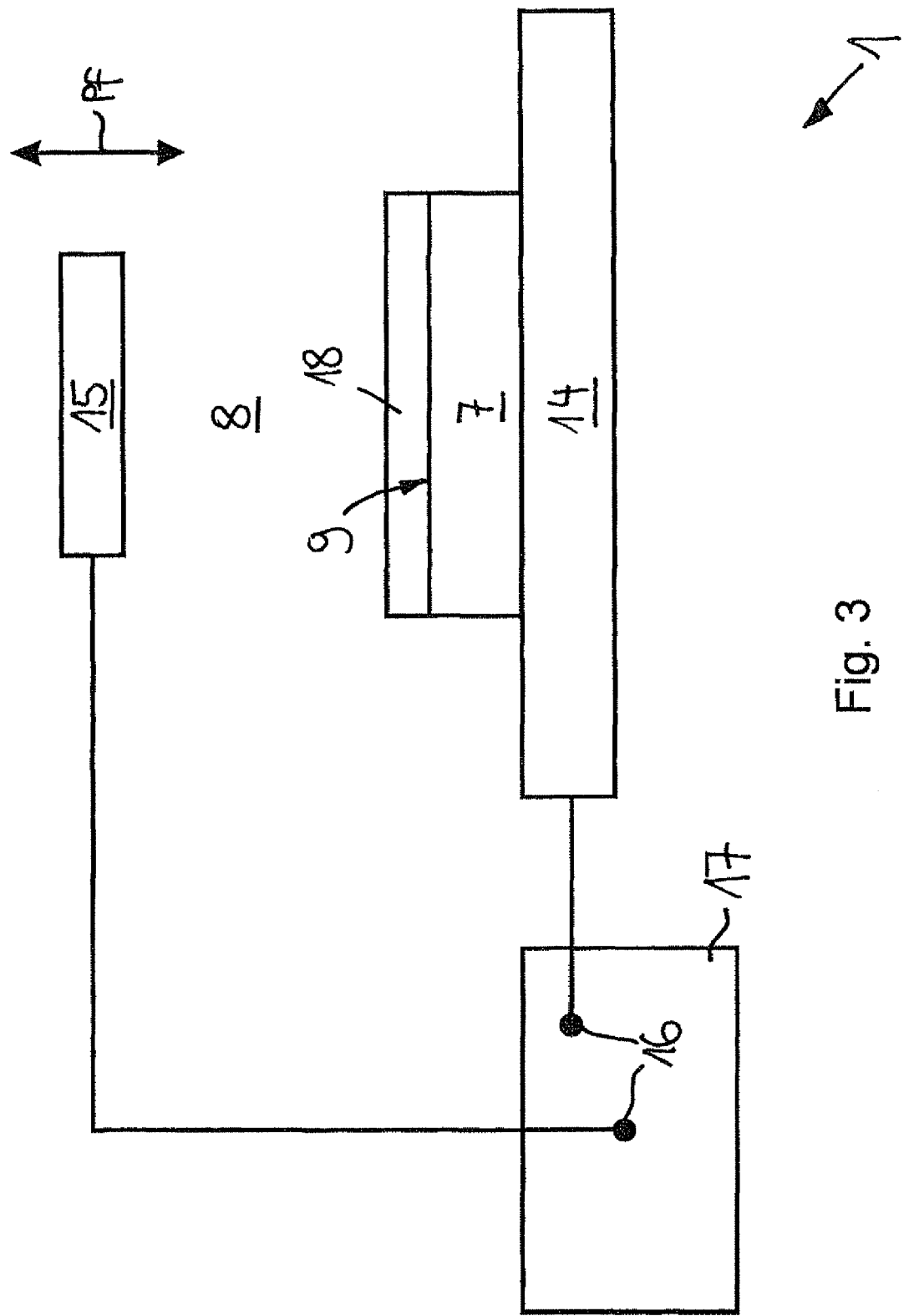
Figure 4:
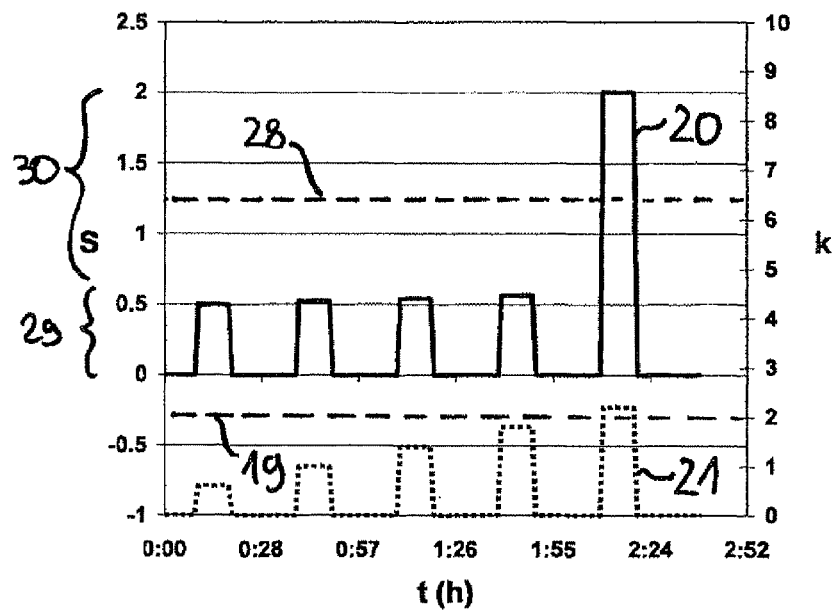
Figure 5:
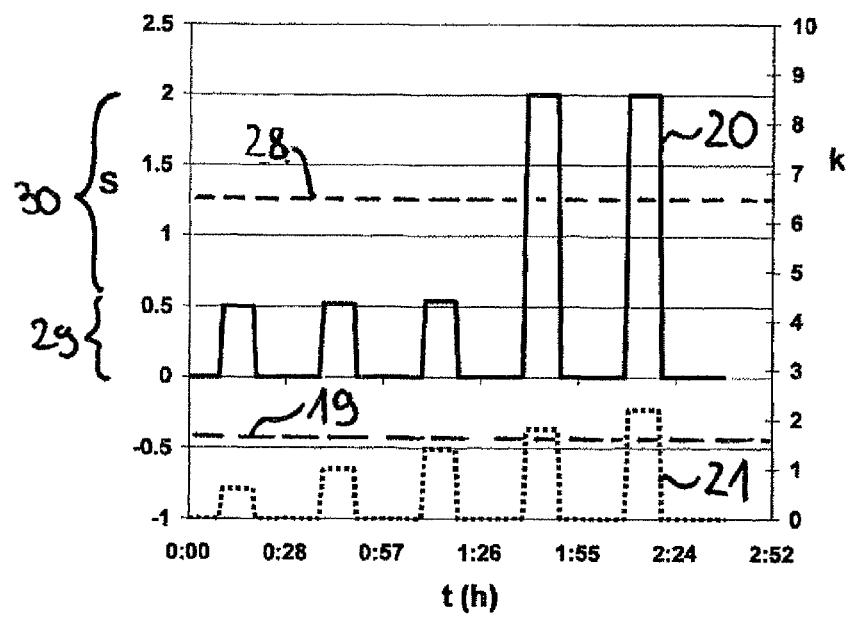
Figure 6:
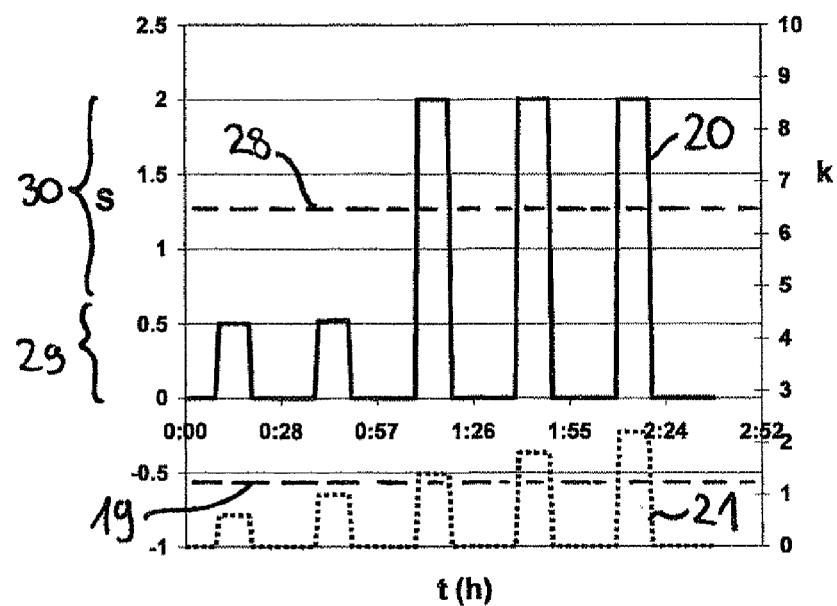
Figure 7:
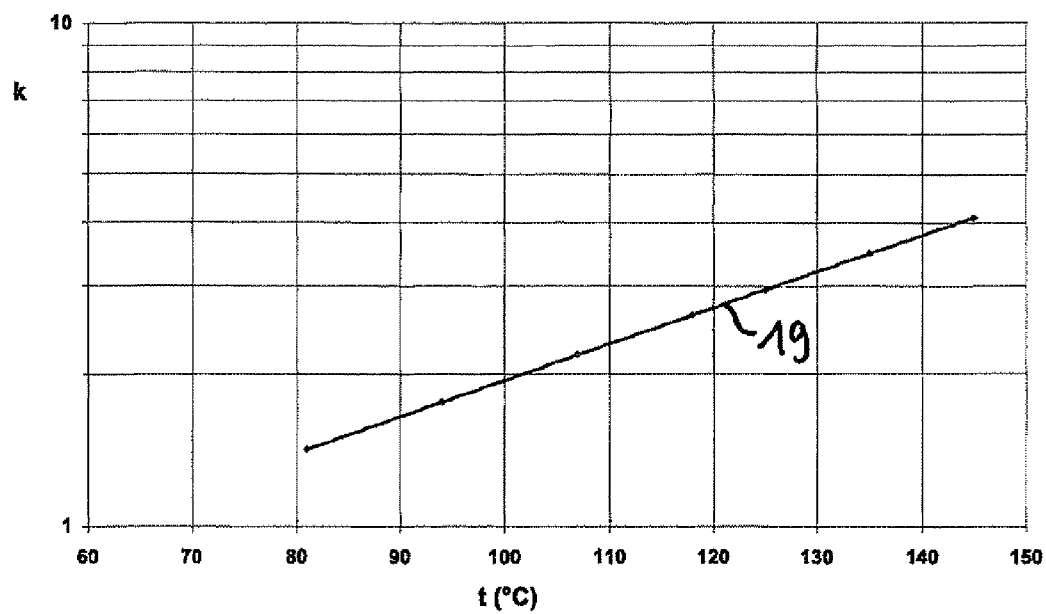
Figure 8:
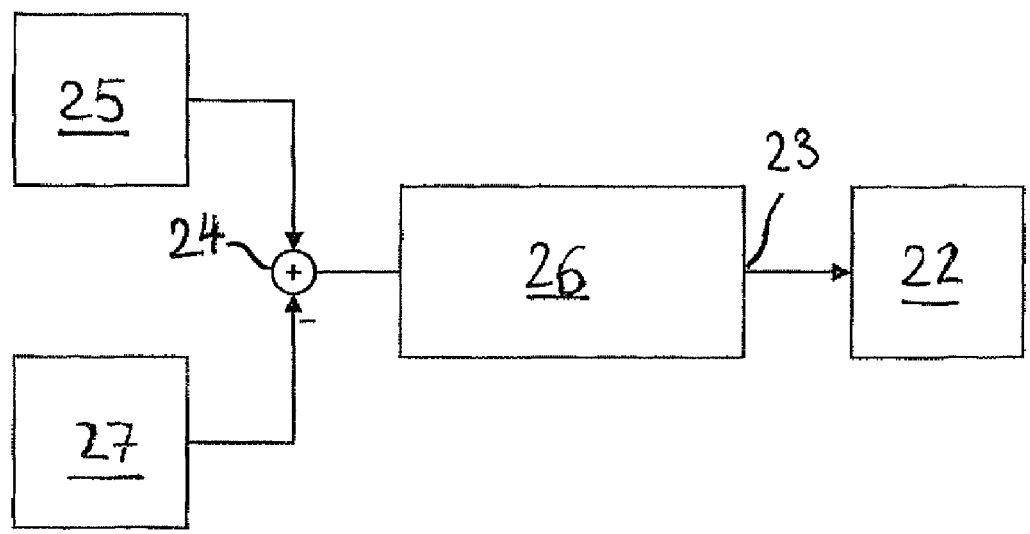

Illustrative embodiments are explained in more detail in the following, with reference to the drawings, wherein:

FIG. 1 a cross-section of a gas sensor that has a SGFET, whose channel is capacitively coupled to a gas-sensitive layer with a passive coating via an air gap, FIG. 2 a cross-section of a gas sensor that has a CCFET, whose sensor electrode is capacitively coupled to a gas-sensitive layer with a passive coating via an air gap, FIG. 3 a cross-section of a gas sensor designed as a Kelvin probe, where the gas-sensitive layer has a passive coating, FIG. 4 a graph illustration of a sensor signal (top curve) and the target gas concentration (bottom curve) in an illustrative embodiment of the gas sensor, whereby the x-axis is time t, the left y-axis is the amplitude S of a potential sensor's sensor signal and the right y-axis is the target gas concentration k, FIG. 5 a similar illustration to FIG. 4 whereby, however, the temperature of the gas sensor is lower than in FIG. 4, FIG. 6 a similar illustration to FIG. 5 whereby, however, the temperature of the gas sensor is lower than in FIG. 5, FIG. 7 a graph illustration of a threshold for the target gas concentration of the gas sensor, whereby the x-axis is the temperature and the y-axis is the threshold, and FIG. 8 a schematic illustration of a control device.

A gas sensor designated in its entirety by 1 in FIG. 1 has a substrate 2, in which a potential sensor 27 is integrated. The potential sensor 27 has a drain 3 and a source 4 that are arranged in an n-doped transistor well. The drain 3 and the source 4 can be made of p-doped silicon, for example. The drain 3 is connected to a drain terminal, which is not shown in any greater detail in this drawing, via electrical conductors. In a corresponding manner, the source 4 is connected to a source terminal. Between drain 3 and source 4 in the substrate 2, a channel 5 is formed, to which an electrically insulating thin oxide layer is applied, which acts as a gate dielectric.

Over the channel 5, a gas-sensitive layer 7 is applied to a substrate 6, which can be made of, for example, a precious metal, particularly platinum or palladium, and is separated from the channel 5 by an air gap 8. The surface area 9 of the gas sensitive layer 7 that is opposite the channel 5 is capacitively coupled to the channel 5 via an air gap 8.

The substrate 6 is connected on both sides of the gas-sensitive layer 7 with the substrate 2 via an electric insulating layer 10. It can be clearly discerned in FIG. 1 that the substrate 6 and the gas-sensitive layer 7 form a suspended gate.

The air gap 4 is connected to the atmosphere surrounding the gas sensor 1 via at least one of the openings, not shown in any greater detail in this drawing. Via this opening, the surface area 9 of the gas-sensitive layer 7 can come in contact with a detectable target gas, namely hydrogen, and a non-target gas, namely an electronegative gas such as atmospheric oxygen. When in contact with the surface area 9 the target gas and the non-target gas adsorb on the surface area 9. Upon the adsorption of the target gas, the electron affinity of the surface area 9 changes which leads to a change in the electrical potential in the channel 5.

In the illustrative embodiment in FIG. 1, the channel 5 is designed as open (ISFET) and is capacitively coupled to the gas-sensitive layer 7 via the thin oxide layer and the air gap 8. It can be clearly discerned that the channel 5 is arranged to the side of the gas-sensitive layer 7 opposite the air gap 8.

In the illustrative embodiment in FIG. 2, the field effect transistor is configured as a CCFET, in which the channel 5 is arranged laterally next to the gas-sensitive layer 7 in the substrate 2 and is covered by a gate electrode 11. To capacitively couple the channel 5 to the gas-sensitive layer 7, the gate electrode 11 is connected, via an electric coupler 12, to a sensor electrode 13, which is arranged on the side of the air gap 8 that is opposite the surface area 9 of the gas-sensitive layer 7 on an insulating layer 10 found on the substrate 2. The insulating layer 10 can be a $SiO_2$ layer, for example. The construction of the SGFET's suspended gate corresponds to FIG. 1.

In the illustrative embodiment in FIG. 3, the gas sensor 1 is designed as a Kelvin probe. The gas-sensitive layer 7 is attached to an electrically conducting substrate 14 and has a surface area 9 on the side opposite the substrate 14, on which the target gas can adsorb. The surface area 9 is separated from an electrode 15 by an air gap 8 and forms an electrical capacitance with it.

The electrode 15 can be brought to oscillate with the help of an actuator that is not shown in any greater detail in this drawing. Thereby, the electrode 15 moves alternately towards and away from the gas-sensitive layer 7 in accordance with the arrow Pf. The electrode 15 and the substrate 14, and respectively the gas-sensitive layer 7, are connected to an evaluation and piloting device 17 with ports 16. This evaluation and piloting device 17 has a potential sensor, not shown in any greater detail, that is connected to the ports 16 for the measurement of electrical potential between the gas-sensitive layer 7 and the electrode 15. The evaluation and piloting device 17 also has a variable voltage supply source connected to the potential sensor via a control connection that is applied via a counter voltage between the potential sensor and the electrode 15 and/or the substrate 15. The counter voltage is chosen so that the potential measured by the potential sensor will average zero.

In the previously described illustrative embodiments of the gas sensor 1, the surface area 9 of the gas-sensitive layer 7 is in each case covered by an electrically insulating coating 18 that is inert to the target gas and that preferably consists of polymethylmethacrylate (PMMA) or polyimide. The coating 18 is bonded to the gas-sensitive layer 7. The coating 18 is configured as a thick layer with an almost constant thickness, preferably between 0.5 µm and 2.5 µm.

The coating 18 is permeable for both the target gas as well as the non-target gas. The coating 18, however, has a different diffusion constant for the target gas than for the non-target gas. The diffusion constants, the target gas and the non-target gas, are coordinated with each other in such a way that the sensitivity of the gas sensor 1 to the target gas increases drastically when the concentration of the target gas crosses a threshold 19 in the presence of the non-target gas. The level of the threshold 19 depends on the temperature.

It is discernable in FIGS. 4 through 6 that, at constant temperatures of target gas concentrations that lay within an initial concentration range that is upwardly limited by the concentration threshold 19 the sensor signal 20 of the potential sensor 27 initially increases logarithmically with the target gas concentration 21. The sensor signal 20 of the potential sensor 27 lies in an initial modulation range 29 in the first concentration area.

In a second concentration range that shares a bottom border with the concentration threshold and is considerably narrower than the first concentration range, the sensor signal 20 increases drastically at a constant temperature. In the second concentration range, the sensor signal 20 lies in a second modulation range 30, in which the measurement sensitivity of the gas sensor 1 is greater than in the first modulation range 29. In a third concentration range that lies above and borders the second concentration range, the sensor signal 20 of the potential sensor 27 remains essentially constant when the temperature is constant at a value that borders the second concentration range.

It is discernable in FIG. 7 that the concentration threshold 19 depends on the temperature of the layer sequence formed by the gas-sensitive layer 7 and the coating 18 and continuously climbs with increasing temperature. The increase occurs almost exponentially with temperature. If necessary, the exponential increase can be linearly approximated in the range relevant for the concentration measurement.

The gas sensors depicted in FIGS. 1 through 3 each have a temperature control unit 22, that is only schematically depicted in FIG. 8, with which the temperature of the gas-sensitive layer 7 and the coating 18 can be adjusted. A control entry for the temperature control unit 22 is connected with a control signal output 23 of a control device that serves to adjust the temperature of the gas-sensitive layer 7 and the coating 18 so that the sensor signal 20 of the potential sensor 27 can be essentially independent of the gas concentration and lies within the second modulation range 30.

The control device has a comparator 24 that has an actual value entry connected to the potential sensor 27 and a set point entry connected to a set point device 25. An output of the comparator 24 is connected to the control signal output 23 via a controller 26. With the help of the set point device 25, a set point 28 is assigned to the set point entry located in the second modulation range 30, thus having a value where the sensor signal (20) of the potential sensor (27) has a target gas concentration above the concentration threshold (19).

In one of the first operating modes for the gas sensor 1, the controller 26 controls the temperature control unit 22 in such a way so that in the event of a discrepancy between the sensor signal 20 of the potential sensor 27 and the set point 28, the temperature of the gas-sensitive layer 7 and the coating 18 is changed in order to reduce the discrepancy. When the sensor signal 20 of the potential sensor 27 agrees with the set point 28, the temperature of the gas-sensitive layer 7 and the coating 18 is a gauge for the target gas concentration.

In a second operating mode, with the help of the temperature control unit 22, the temperature of the gas-sensitive layer 7 and the coating 18 are adjusted to a constant value. Alternately, the temperature control unit 22 can also be turned off in the second operating mode, so that the temperature of the gas sensor 1 then approximately reflects the ambient air temperature. The second operating mode is always then activated when the temperature detected by the controller 26 falls below a predetermined minimum temperature. This temperature can lie between 60-80° C., for example.

In the second operating mode, the target gas concentration is established based on the signal value of the sensor signal 20 of the potential sensor 27 and based on parameters that could, for example, exist in the form of a characteristic curve. In the second operating mode, the signal analysis essentially reflects that of a conventional gas sensor. As soon as the minimum temperature is exceeded, the mode switches over so as to determine the target gas concentration based on the preset temperature. Thus, the first operating mode is utilized for high target gas concentrations and the second operating mode for lower target gas concentrations.

The first operating mode is preferably chosen when the target gas concentration is between 1% and 4%. The appropriate concentration range can be determined through experimentation. In this mode, a nearly exponential correlation between temperature and target gas concentration results. Thereby, the gas sensor 1 according to the invention enables a clearly improved solution in comparison with a conventional gas sensor.

The invention claimed is:

1. A gas sensor with at least one gas-sensitive layer that has at least one surface area in which the electron affinity depends on the concentration of a target gas brought in contact with the surface area and with at least one electrical potential sensor that is capacitively coupled with the surface area via an air gap, wherein the surface area of the gas-sensitive layer is covered by an electric insulating coating that is inert to the target gas and is bonded to the gas-sensitive layer wherein said electric insulating coating is permeable on the surface layer for both the target gas and a different, non-target gas, wherein said electric insulating coating has different diffusion constants for the target gas and the non-target gas, and wherein the measurement sensitivity of the gas sensor increases for the target gas when the target gas concentration exceeds a predetermined concentration threshold in the presence of the non-target gas.

2. The gas sensor, as in claim 1, wherein the target gas is hydrogen, and the non-target gas is oxygen.

3. The gas sensor, as in claim 1, wherein the coating contains at least one polymer.

4. The gas sensor, as in claim 3, wherein the polymer is polyimide.

5. The gas sensor, as in claim 3, wherein the polymer is polymethylmethacrylate.

6. The gas sensor, as in claim 1, wherein the coating is a lacquer.

7. The gas sensor, as in claim 1, wherein the thickness of the coating is between 0.3 µm and 4 µm.

8. The gas sensor, as in claim 1, wherein the level of the concentration threshold depends on the temperature of the gas-sensitive layer and the coating and that the gas sensor has a temperature control unit, preferably a heater, for setting the temperature of the gas-sensitive layer and the coating.

9. The gas sensor, as in claim 1, further including a control device with an actual value entry connected to the potential sensor, a set point entry connected to a set point device, and a control signal output connected to a temperature control unit, wherein, to adjust the concentration threshold to the target gas concentration, a set point can be assigned to the set point entry, which has a value where the sensor signal of the potential sensor lies at the concentration threshold and/or a target gas concentration that lies above the concentration threshold.

10. The gas sensor, as in claim 1, wherein the gas-sensitive layer is platinum or palladium.

11. The gas sensor, as in claim 1, wherein the potential sensor is a field effect transistor with a substrate, on which a drain and a source are arranged, that a channel is formed between drain and source, and that the channel is capacitively coupled to the surface area of the gas-sensitive layer directly via the air gap or indirectly via a gate electrode, acting with the channel, and a sensor electrode that is conductively connected with the gate electrode.

12. The gas sensor, as in claim 1, wherein it is designed as a Kelvin probe, in which the potential sensor is capacitively coupled to the surface area of the gas-sensitive layer via an electrode that is separated from the surface area of the gas-sensitive layer by the air gap and that can be moved towards and away from the gas-sensitive layer.

13. The gas sensor according to claim 1 wherein the target gas is a reducing gas, and the non-target gas is an electronegative gas.

14. The gas sensor, as in claim 1, wherein the thickness of the coating is between 0.5 μm and 2.5 μm.

* * * * *